United States Patent
Lee et al.

(10) Patent No.: US 11,359,173 B2
(45) Date of Patent: Jun. 14, 2022

(54) MASS-CULTIVATION SYSTEM FOR MICROALGAE

(71) Applicant: KOREA INSTITUTE OF INDUSTRIAL TECHNOLOGY, Chungcheongnam-do (KR)

(72) Inventors: Uen Do Lee, Daejeon (KR); Won Yang, Gyeonggi-do (KR); Byung Ryeul Bang, Seoul (KR); Su Ji Jeon, Jeollabuk-do (KR)

(73) Assignee: KOREA INSTITUTE OF INDUSTRIAL TECHNOLOGY, Chungcheongnam-do (KR)

( * ) Notice: Subject to any disclaimer, the term of this patent is extended or adjusted under 35 U.S.C. 154(b) by 0 days.

(21) Appl. No.: 16/904,095

(22) Filed: Jun. 17, 2020

(65) Prior Publication Data

US 2020/0339924 A1   Oct. 29, 2020

Related U.S. Application Data

(62) Division of application No. 15/322,511, filed as application No. PCT/KR2015/001338 on Feb. 10, 2015, now abandoned.

(30) Foreign Application Priority Data

Jun. 30, 2014   (KR) .................. 10-2014-0080836

(51) Int. Cl.
*C12M 1/00* (2006.01)
*C12M 1/26* (2006.01)
*C12M 1/42* (2006.01)

(52) U.S. Cl.
CPC ............ *C12M 21/02* (2013.01); *C12M 23/58* (2013.01); *C12M 29/18* (2013.01); *C12M 31/10* (2013.01); *C12M 33/00* (2013.01); *C12M 35/04* (2013.01); *C12M 47/02* (2013.01); *C12M 47/20* (2013.01)

(58) Field of Classification Search
CPC ...................................................... C12M 21/02
See application file for complete search history.

(56) References Cited

U.S. PATENT DOCUMENTS

2012/0083026 A1* 4/2012 Hader ................... B01D 53/85
435/266

* cited by examiner

*Primary Examiner* — Jonathan M Hurst
(74) *Attorney, Agent, or Firm* — McNees Wallace & Nurick LLC

(57) ABSTRACT

Disclosed is a mass-cultivation system for microalgae, including a reactor that contains a cultivation liquid in the interior thereof, wherein the liquid includes functional particles. According to the mass-cultivation system for microalgae according to the present invention, because various functions that are necessary for cultivation of microalgae may be uniformly distributed in a cultivation liquid by allowing functional particles having various functions to flow in the cultivation liquid, a suitable environment may be created based on the cultivation of a large amount of microalgae and the growth of microalgae so that a high efficiency cultivation system may be realized while the problems of mass-cultivation of an existing cultivation system may be solved.

18 Claims, 3 Drawing Sheets

(a) (b) (c) (d) (e)

(f)

(g)

MASS-CULTIVATION SYSTEM FOR MICROALGAE

CROSS-REFERENCE TO RELATED APPLICATION

This application claims priority from and the benefit under 35 U.S.C. § 119(a) of Korean Patent Application No. 10-2014-0080836, filed on Jun. 30, 2014 and benefit under 35 U.S.C. § 120 of U.S. patent application Ser. No. 15/322,511, filed Dec. 28, 2016, each of which is hereby incorporated by reference for all purposes as if fully set forth herein.

BACKGROUND OF THE INVENTION

1. Field of the Invention

The present invention relates to cultivation of microalgae, and more particularly to a mass-cultivation system for microalgae that provides an environment that is suitable for cultivation of microalgae to mass-cultivate microalgae.

2. Description of the Prior Art

As biomasses may be easily obtained from the nature and may be resources that may be consistently produced through a photosynthetic process that uses solar energy, water, and materials such as carbon dioxide, biofuels that are produced by using the biomasses also may be consistently produced. In particular, the efficiency of using microalgae is about 25 times as high as that of the plants and the carbon dioxide fixing capacity of the microalgae is also about 15 times as high as that of the plants, so the productivity for biomasses of the microalgae is also 5 to 10 times as high as that of the plants. Further, because fat may occupy a maximum of 70% of the body according to a cultivation condition, the output of fat per unit area is 50 to 100 times as high as that of the plants. In recent years, due to the development of engineering technologies, studies for enhancing the growth speeds and recovery rates of microalgae have been spotlighted. It is important to create an optimum environment in which microalgae may grow in order to enhance the growth speeds and recovery rates of the microalgae, and in the environment, it is very important to supply a light source and $CO_2$ that are suitable for photosynthesis of microalgae and nutrients necessary for growth of the microalgae. Accordingly, as a recently published microalgae cultivation related technology, Korean Patent Application Publication No. 2011-0085428 discloses a technology of supplying light from the outside to a transparent reactor to activate photosynthesis, but it is difficult to mass-cultivate microalgae because light from an external light source completely reach the center of the reactor as the size of the reactor increases.

As a technology for improving the problem, Japanese Patent Application Publication No. 2014-039491 discloses a technology of allowing microalgae in a reactor to flow in a pipe of a specific diameter and irradiating light into the pipe to constantly supply light to the microalgae that flows in the pipe regardless of the size of the reactor, but additional facilities, such as a pipe for supplying light and a pump for forcing the microalgae to flow, in addition to the reactor are necessary. Also, as a similar technology, Korean Patent Application Publication No. 2013-0029586 discloses a technology of condensing light with a condenser, and distributing the condensed light by using a light distributor, supplying the distributed light to pipe-shaped light guides in a reactor, but the number of the light guides increases as the size of the reactor increases, and accordingly, the intensity of light that is naturally distributed becomes weaker and thus it is difficult to apply this technology to mass-cultivation of microalgae. Further, in addition to the light supply problem, it is very difficult to uniformly distribute various factors, such as nutrients and $CO_2$, which are necessary for cultivation of microalgae if the size of a reactor for mass-cultivation of microalgae increases, and it is also difficult to recover microalgae that have been mass-cultivated.

Further, in spite that various factors for microalgae have to be changed based on the growth steps, this issue has not been considered at all.

SUMMARY OF THE INVENTION

Accordingly, the present invention has been made in an effort to solve the above-mentioned problems, and provides a mass-cultivation system for microalgae that may expand the size of a reactor and mass-cultivate microalgae by uniformly distributing various factors that are necessary for growth of microalgae in a cultivation liquid, and may improve the growth speed of the microalgae by adjusting factors according the growth of the microalgae, thereby efficiently cultivating and recovering the microalgae.

In accordance with an aspect of the present invention, there is provided a mass-cultivation system for microalgae, including a reactor that contains a cultivation liquid in the interior thereof, wherein the liquid includes functional particles.

It is preferable that the mass-cultivation system further includes a recycling unit and a recover unit that are fluid-communicated with the reactor, and the functional particles are introduced into the recycling unit such that functions thereof are recycled.

It is preferable that the functional particles includes one or more of light supply particles, nutrient supply particles, harmful substance adsorption particles, $CO_2$ supply particles, and microalgae recovery particles.

It is preferable that each of the light supply particles, the nutrient supply particles, the harmful substance adsorption particles, and the $CO_2$ supply particles includes a hollow capsule that defines an outer side of the particle.

It is preferable that the interiors of the capsules of the light supply particles are filled with a light emitting material.

It is preferable that the interiors of the capsules of the nutrient supply particles are filled with a nutrient supply material.

It is preferable that the interiors of the capsules of the $CO_2$ supply particles are filled with $CO_2$.

It is preferable that the interiors of the capsules of the harmful substance adsorption particles are filled with a harmful substance adsorption material.

It is preferable that a plurality of bosses are formed on surfaces of the microalgae recovery particles to capture cultivated microalgae.

It is preferable that one or more of the light supply particles, the nutrient supply particles, the harmful substance adsorption particles, the $CO_2$ supply particles, and the microalgae recovery particles have a magnetism, and the recycling unit or the recovery unit has a magnetism so that the particles having a magnetism are separated to flow to the recycling unit or the recovery unit.

It is preferable that the light supply particles, the nutrient supply particles, the harmful substance adsorption particles, the $CO_2$ supply particles, and the microalgae recovery particles have a specific gravity in a predetermined range.

It is preferable that the light supply particles, the nutrient supply particles, the harmful substance adsorption particles, the $CO_2$ supply particles, and the microalgae recovery particles have different specific gravities in the predetermined range so that the particles are separated to flow to the recycling unit or the recovery unit.

It is preferable that two or more of the light supply particles, the nutrient supply particles, the harmful substance adsorption particles, the $CO_2$ supply particles, and the microalgae recovery particles are connected to each other by a connection line.

It is preferable that the recycling unit includes a light source or a power supply unit, and the light supply particles flow to the recycling unit such that the light emitting material filled in the light supply particles is recycled by the light source or the power supply unit and is reintroduced into the reactor.

It is preferable that the recycling unit contains a light emitting material, a harmful substance adsorption material, or $CO_2$, and the nutrient supply particles, the harmful substance adsorption particles, or the $CO_2$ supply particles flow to the recycling unit such that the nutrient supply material, the harmful substance adsorption material, or $CO_2$ contained in the recycling unit are refilled and are reintroduced into the reactor.

It is preferable that the microalgae recovery particles flow to the recovery unit and are reintroduced into the reactor, and the recovery unit includes a freezer unit or a drying unit that freezes or dries the microalgae captured by the microalgae recovery particles.

It is preferable that the recovery unit separates the captured microalgae from the microalgae recovery particles by rotating the frozen or dried microalgae recovery particles or applying ultrasonic waves or vibration to the microalgae recovery particles.

It is preferable that the reactor includes a primary reactor, a secondary reactor that is fluid-communicated with the primary reactor, and a tertiary reactor that is fluid-communicated with the secondary reactor, recycling unit includes a first recycling unit that is fluid-communicated with the primary reactor, a second recycling unit that is fluid-communicated with the secondary reactor, and a third recycling unit that is fluid-communicated with the tertiary reactor, and the recovery unit is fluid-communicated with the tertiary recycling unit.

It is preferable that the light supply particles, the nutrient supply particles, the $CO_2$ supply particles, and the harmful substance adsorption particles circulate between the primary reactor and the first recycling unit, and between the secondary reactor and the second recycling unit, and the microalgae recovery particles circulate between the tertiary reactor and the third recycling unit.

It is preferable that the amounts of the light emitting material, the nutrient supply material, $CO_2$, and the harmful substance adsorption material that are filled in the light supply particles, the nutrient supply particles, the $CO_2$ supply particles, and the harmful substance adsorption material that circulate the secondary reactor and the second recycling unit may be larger than the amounts of the light emitting material, the nutrient supply material, $CO_2$, and the harmful substance adsorption material that are filled in the light supply particles, the nutrient supply particles, the $CO_2$ supply particles, and the harmful substance adsorption material that circulate the primary reactor and the first recycling unit, It is preferable that each of the first and second recycling units includes a light source or a power supply unit, and the light supply particles flow to the first and second recycling units such that the light emitting material filled in the light supply particles is recycled by the light source or the power supply unit and is reintroduced into the primary reactor and the secondary reactor.

It is preferable that the first and second recycling units contain a light emitting material, a harmful substance adsorption material, or $CO_2$, and the nutrient supply particles, the harmful substance adsorption particles, or the $CO_2$ supply particles flow to the first and second recycling units such that the light emitting material, the harmful substance adsorption material or $CO_2$ contained in the first and second recycling units is refilled and is reintroduced into the primary reactor 110 and the secondary reactor.

It is preferable that the microalgae recovery particles flow to the recovery unit and are reintroduced into the tertiary reactor, and the recovery unit includes a freezer unit or a drying unit that freezes or dries the microalgae captured by the microalgae recovery particles.

BRIEF DESCRIPTION OF THE DRAWINGS

The above and other objects, features and advantages of the present invention will be more apparent from the following detailed description in conjunction with the accompanying drawings, in which.

DETAILED DESCRIPTION OF THE EXEMPLARY EMBODIMENTS

The elements constituting a mass-cultivation system for microalgae according to the present invention may be integrally used or separately used as occasion demands. Further, some elements may be omitted according to the usage of the mass-cultivation system.

A preferred embodiment of a mass-cultivation system for microalgae according to the present invention will be described with reference to FIGS. 1 to 4. It should be noted that the drawings are not to precise scale and may be exaggerated in thickness of lines or size of components for descriptive convenience and clarity. In addition, terms used herein are defined by taking functions of the present invention into account and can be changed according to user or operator custom or intention. Therefore, definition of the terms should be made according to the overall disclosure set forth herein.

Hereinafter, a mass-cultivation system for microalgae according to an embodiment of the present invention will be described in detail with reference to FIGS. 1 to 4.

Figure 1:
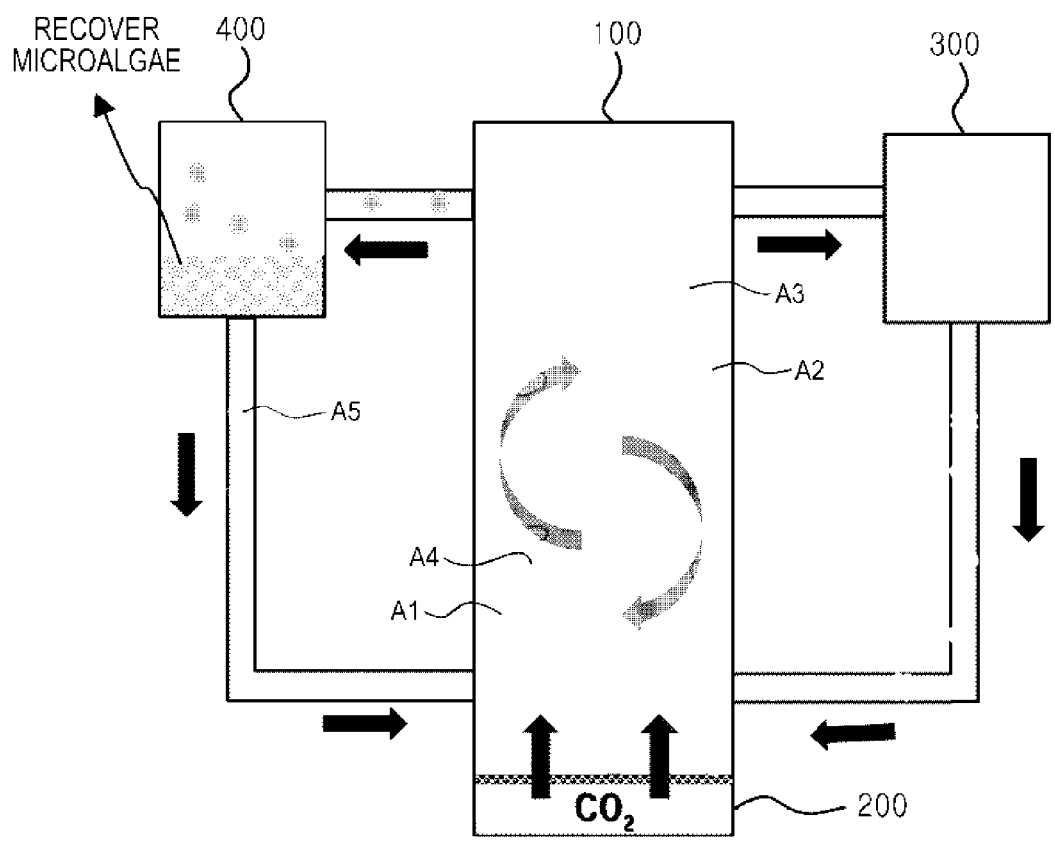
FIG. 1 is a schematic view of a mass-cultivation system for microalgae according to an embodiment of the present invention.

FIG. 1 is a schematic view of a mass-cultivation system for microalgae according to an embodiment of the present invention.

As illustrated in FIG. 1, the mass-cultivation system for microalgae according to an embodiment of the present invention includes a reactor 100, a recycling unit 300, and a recovery unit 400.

It is preferable that the reactor 100 contain a cultivation liquid for cultivating microalgae and have a hollow cylindrical shape such that the cultivation liquid smoothly flows in the reactor 100, and it is more preferable that a gas supply 200 is located under the reactor 100 to supply gas into the reactor 100 to allow the cultivation liquid to flow and the supplied gas is a gas containing $CO_2$.

The cultivation liquid includes functional particles A.

The functional particles A will be described with reference to FIGS. 2 and 3.

Figure 2:
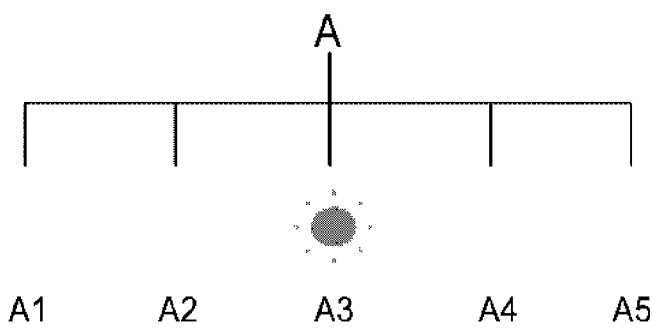
FIG. 2 is a view illustrating an example of kinds of functional particles A according to the present invention.

FIG. 2 is a view illustrating an example of kinds of functional particles A according to the present invention. FIG. 3 is a view illustrating connection and integration of functional particles A according to the present invention.

The functional particles A give a state or a factor that may contribute to a series of processes including the growth or recovery of microalgae when the microalgae are cultivated, and accordingly, are not limited to a specific embodiment, which will be described below.

A plurality of functional particles A are included in the cultivation liquid to flow together with the cultivation liquid, and accordingly, provide various functions that are helpful to the cultivation of the microalgae.

For example, as illustrated in FIG. 2, the functional particles A may include light supply particles A1, nutrient supply particles A2, harmful substance adsorption particles A3, $CO_2$ supply particles A4, and microalgae recovery particles A5.

Further, it may be preferable that the functional particles A have a specific gravity in a predetermined range to be uniformly distributed in the cultivation liquid without being deposited or floating in the cultivation liquid, in order to effectively provide the functions, such that the specific gravity of the functional particles A is relatively close to the specific gravity of the cultivation liquid, and for example, it is more preferable that the specific gravity of the functional particles be the same as or higher than the specific gravity of the cultivation liquid so that the particles may be easily controlled. As described above, when the cultivation liquid include various kinds of functional particles A, they may have different specific gravities within a predetermined specific range or have different sizes, and accordingly, the functional particles A may selectively flow according to the different specific gravities or sizes so that the particles may be introduced into the recycling unit 300 after being sorted.

Further, the functional particles A may selectively have a magnetic property according to the kinds thereof to selectively flow according to whether the functional particles have a magnetic property.

In more detail, as an example, it is preferable that the light supply particles A1, the nutrient supply particles A2, the harmful substance adsorption particles A3, and the $CO_2$ supply particles A4 of the functional particles A include hollow capsules that constitute outer sides thereof.

A light emitting material that absorbs light and emits light may be filled in the interiors of the capsules of the light supply particles A1. Further, it may be preferable that the capsule is transparent.

The capsules of the nutrient supply particles A2 may be filled with a nutrient material that is helpful to the growth of microalgae, and the nutrient material is not limited but may include nutrient materials including nitrogen, phosphor, or a composite thereof.

The capsules of the harmful substance adsorption particles A3 may be filled with an adsorption material for adsorbing a microalgae growth hampering substance (for example, ammonia based nitrogen of a high concentration) that is generated by a metabolism when microalgae are cultivated, and the adsorption material is not limited but for example, may be an adsorption material including active carbon or microorganisms that decompose harmful substances.

The capsules of the $CO_2$ supply particles A4 may be filled with $CO_2$ that is necessary for photosynthesis of microalgae, and the phase of $CO_2$ is not limited but, for example, may be dry ice for supplying $CO_2$.

Bosses or cilia may be formed on the surfaces of the microalgae recovery particles A5 or the surfaces of the microalgae recovery particles A5 may be formed of a mesh material such that the microalgae in the reactor 100 may be easily recovered, and accordingly, the microalgae that have grown in the reactor 100 to a specific size or more may be attached on or captured by the particles.

Further, in order to efficiently provide functions of the functional particles A, a plurality of through-holes may be punched on the surfaces of the functional particles A, and accordingly, the materials filled in the functional particles A may be discharged.

Figure 3:
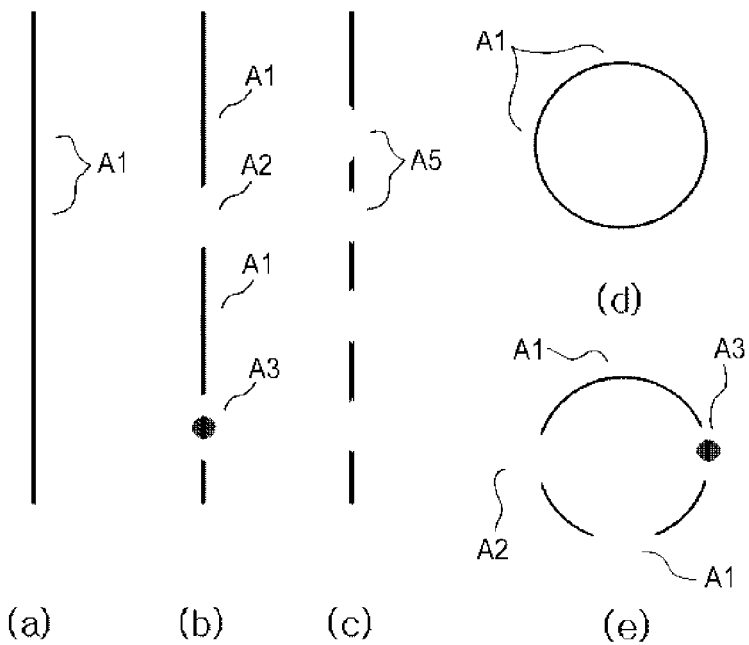
FIG. 3 is a view illustrating connection and integration of functional particles A according to the present invention.
Figure 3:
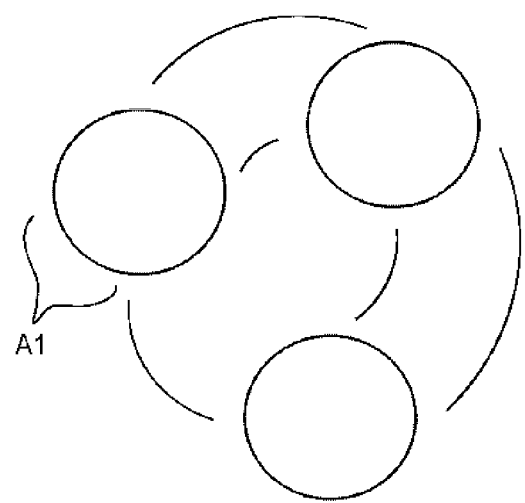
Figure 3:
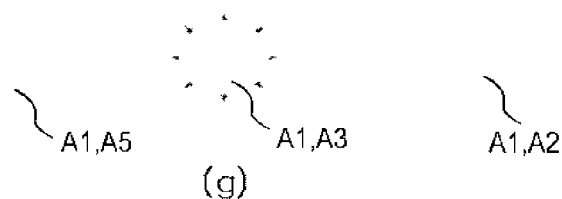

Further, as illustrated in FIG. 3, two or more identical or different functional particles A may be connected to each other by a connection line, and the connection form is not specially limited but may include a line form, a circular form, or a combination thereof (see FIGS. 3A to 3F), and the two or more functional particles A may be integrally formed. For example, the light supply particles A1 and the microalgae recovery particles A5, the adsorption particles A3 and the nutrient supply particles A2, or other combinations may be integrally formed (see FIG. 3G). Accordingly, the sizes of the functional particles A may be reduced, and functional particles A that may flow or be recovered more conveniently may be implemented.

Further, in addition to the functional particles A, an impact absorption liquid may be added to adjust a pH of the cultivation liquid, and particles in which a heat emitting material or a heat absorbing material may be filled to adjust the temperature of the cultivation liquid also may be included.

The recycling unit 300 is fluid-communicated with the reactor 100, the functional particles A, of which the functions have been degraded after flowing in the reactor 100, are introduced into the recycling unit 300 and then is introduced into the reactor 100 again after the functions thereof are recycled, and the functional particles A are recirculated after the process is repeated. That is, the recycling unit 300 restores the degraded functions of the functional particles A.

In more detail, in the case of the light supply particles A1, a light/power supply unit is provided in the recycling unit 300 to supply light to the light emitting material filled in the light supply particles A1 introduced into the recycling unit 300 in order to recycle the light emitting material, and in the case of the nutrient supply particles A2, the $CO_2$ supply particles A4, and the harmful substance adsorption particles A3, the nutrient supply material, $CO_2$, and the harmful substance adsorption material contained in the recycling unit 300 may be refilled and recycled.

Further, when the recycling unit 300 has a magnetism, and as described above, some functional particles A have a magnetism, the functional particles A may selectively flow to the recycling unit 300 to be recycled. Further, although not illustrated, desired functional particles A may selectively flow into the recycling unit 300 to be recycled according to the specific gravity of the functional particles A by varying the installation height of the recycling unit 300. Accordingly, the functional particles A may be efficiently controlled.

The recovery unit 400 is fluid-communicated with the reactor 100, and the microalgae, which have cultivated in the reactor 100 and have grown to a specific size or more, are introduced together the cultivation liquid and are separated by the recovery unit 400 to be recovered.

The microalgae recovery particles A5 may be introduced to the recovery unit 400 due to the difference between the magnetisms or specific gravities, and as described above, the microalgae may be attached on or captured by the bosses of the surfaces of the microalgae so that the recovery rate of the microalgae may be improved. The method of recovering the microalgae is not limited, but for example, the recovery unit 400 includes a freezer unit or a drying unit (not illustrated) for freezing or drying the interior of the recovery unit 400 so that the microalgae recovery particles A5, on which the microalgae is attached or captured, may be frozen or dried and accordingly, the microalgae, which are captured or attached through rotation thereof, or by applying ultrasonic waves or vibration, may be separated from the microalgae recovery particles A5 and be recovered.

Hereinafter, a mass-cultivation system for microalgae according to another embodiment of the present invention will be described with reference to FIG. 4.

In the following description, a difference from the first embodiment will be mainly described for understanding of the present invention and convenience of description, and the same configuration or operations thereof will not be described.

Figure 4:
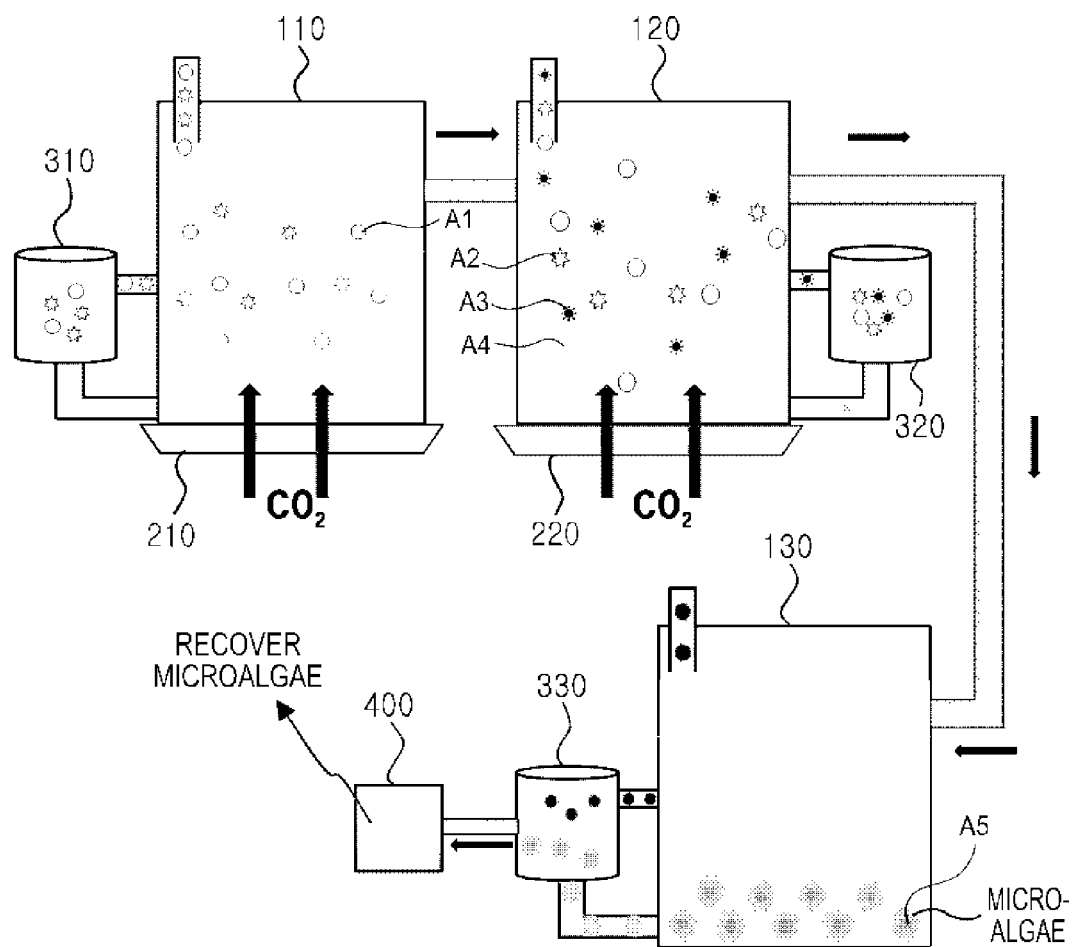
FIG. 4 is a schematic view of a mass-cultivation system for microalgae according to another embodiment of the present invention.

FIG. 4 is a schematic view of a mass-cultivation system for microalgae according to another embodiment of the present invention.

As illustrated in FIG. 4, the reactor 100 of the present embodiment includes a primary reactor 110, a secondary reactor 120 that is fluid-communicated with the primary reactor 110, and a tertiary reactor 130 that is fluid-communicated with the secondary reactor 120, and gas supplies 210, 220 that supply gas into the reactor 100 are provided below the primary reactor 110 and the secondary reactor 120.

Further, the recycling unit 300 may include a first recycling unit 310 that is fluid-communicated with the primary reactor 110, a second recycling unit 320 that is fluid-communicated with the secondary reactor 120, and a third recycling unit 330 that is fluid-communicated with the tertiary reactor 130.

Further, the recovery unit 400 may be fluid-communicated with the third recycling unit 330.

In the present embodiment, three reactors 110, 120, 130 are provided to optimize a cultivation condition according to the growth of microalgae, and the functional particles A may be optimized in the cultivation condition as they selectively flow in the reactors 110, 120, 130 and the recycling unit 300.

For example, the light supply particles A1, the nutrient supply particles A2, the $CO_2$ supply particles A4, and the harmful substance adsorption particles A3 may circulate between the primary reactor 110 and the first recycling unit 310, and between the secondary reactor 120 and the second recycling unit 320, and the microalgae recovery particles A5 may circulate between the tertiary reactor 130 and the third recycling unit 330.

Further, the amounts of the light emitting material, the nutrient supply material, $CO_2$, and the harmful substance adsorption material that are filled in the light supply particles A1, the nutrient supply particles A2, the $CO_2$ supply particles A4, and the harmful substance adsorption material A3 that circulate the secondary reactor 120 and the second recycling unit 320 may be larger than the amounts of the light emitting material, the nutrient supply material, $CO_2$, and the harmful substance adsorption material that are filled in the light supply particles A1, the nutrient supply particles A2, the $CO_2$ supply particles A4, and the harmful substance adsorption material A3 that circulate the primary reactor 110 and the first recycling unit 310, or may have a higher strength (for example, filling of a light emitting material having a high intensity of illumination). The configuration is more complex than that of the first embodiment, but may obtain a higher cultivation effect.

This is because the functions that are necessary according to the growth degree of the microalgae increases, that is, a higher recovery effect may be obtained by cultivating the microalgae while satisfying the functions that are necessary at the initial stage of the cultivation of microalgae in the primary reactor 110, at the initial stage of cultivation, by cultivating while the grown microalgae flow to the secondary reactor 120 if the microalgae are grown to a degree, by allowing more efficient cultivation of the microalgae that have grown to a degree by increasing the amount of materials filled in the functional particles A in correspondence as the amount of photosynthesis increases and the metabolic becomes active, and by intensively separating and recovering the microalgae that have grown such that they may be recovered by allowing the microalgae to flow to the tertiary reactor 130.

According to the mass-cultivation system for microalgae according to the present invention, because various functions that are necessary for cultivation of microalgae may be uniformly distributed in a cultivation liquid by allowing the functional particles having various function to flow in the cultivation liquid, a suitable environment may be created based on the cultivation of a large amount of microalgae and the growth of microalgae so that a high efficiency cultivation system may be realized while the problems of mass-cultivation of an existing cultivation system may be solved.

Although the preferred embodiments of the present invention have been described, it will be understood by those skilled in the art that the present invention can be variously corrected and modified without departing from the spirit and scope of the present invention claimed in the claims.

What is claimed is:

1. A mass-cultivation system for microalgae, comprising:
   a reactor that contains a cultivation liquid in the interior thereof;
   a recycling unit that is fluid-communicated with the reactor; and
   a recovery unit that is fluid-communicated with the reactor;
   wherein the liquid comprises functional particles; and
   wherein the recycling unit includes a receiving connection from the reactor and a returning connection to the reactor;
   wherein the recovery unit includes a receiving connection from the reactor and a returning connection to the reactor;
   wherein the functional particles comprise one or more of light supply particles, nutrient supply particles, harmful substance adsorption particles, $CO_2$ supply particles, and microalgae recovery particles,
   wherein a plurality of bosses is formed on surfaces of the microalgae recovery particles to capture cultivated microalgae,
   wherein the functional particles are introduced into the recycling unit by the receiving connection such that functions thereof are recycled, and then the functional particles are introduced into the reactor from the recycling unit by the returning connection, wherein the recovery unit comprises a freezer unit or a drying unit that freezes or dries the microalgae captured by the microalgae recovery particles, and wherein the recovery unit separates the captured microalgae from the microalgae recovery particles by rotating the frozen or dried microalgae recovery particles.

2. The mass-cultivation system for microalgae of claim 1, wherein the microalgae recovery particles flow to the recovery unit and are reintroduced into the reactor.

3. The mass-cultivation system for microalgae of claim 1, wherein each of the light supply particles, the nutrient supply particles, the harmful substance adsorption particles, and the $CO_2$ supply particles comprises a hollow capsule that defines an outer side of the particle.

4. The mass-cultivation system for microalgae of claim 3, wherein the interiors of the capsules of the light supply particles are filled with a light emitting material.

5. The mass-cultivation system for microalgae of claim 1, wherein one or more of the light supply particles, the nutrient supply particles, the harmful substance adsorption particles, the $CO_2$ supply particles, and the microalgae recovery particles have a magnetism, and wherein the recycling unit or the recovery unit has a magnetism so that the particles having a magnetism are separated to flow to the recycling unit or the recovery unit.

6. The mass-cultivation system for microalgae of claim 1, wherein the light supply particles, the nutrient supply particles, the harmful substance adsorption particles, the $CO_2$ supply particles, and the microalgae recovery particles have a specific gravity in a predetermined range.

7. The mass-cultivation system for microalgae of claim 6, wherein the light supply particles, the nutrient supply particles, the harmful substance adsorption particles, the $CO_2$ supply particles, and the microalgae recovery particles have different specific gravities in the predetermined range so that the particles are separated to flow to the recycling unit or the recovery unit.

8. The mass-cultivation system for microalgae of claim 4, wherein the recycling unit comprises a light source or a power supply unit, and wherein the light supply particles flow to the recycling unit such that the light emitting material filled in the light supply particles is recycled by the light source or the power supply unit and is reintroduced into the reactor.

9. The mass-cultivation system for microalgae of claim 1, wherein the reactor comprises: a primary reactor, a secondary reactor that is fluid-communicated with the primary reactor, and a tertiary reactor that is fluid-communicated with the secondary reactor, wherein the recycling unit comprises: a first recycling unit that is fluid-communicated with the primary reactor, a second recycling unit that is fluid-communicated with the secondary reactor, and a third recycling unit that is fluid-communicated with the tertiary reactor, and wherein the recovery unit is fluid-communicated with the third recycling unit.

10. The mass-cultivation system for microalgae of claim 9, wherein each of the light supply particles, the nutrient supply particles, the harmful substance adsorption particles, and the $CO_2$ supply particles comprises a hollow capsule that defines an outer side of the particle.

11. The mass-cultivation system for microalgae of claim 10, wherein the interiors of the capsules of the light supply particles are filled with a light emitting material.

12. The mass-cultivation system for microalgae of claim 9, wherein one or more of the light supply particles, the nutrient supply particles, the harmful substance adsorption particles, the $CO_2$ supply particles, and the microalgae recovery particles have a magnetism, and wherein the recycling units or the recovery unit has a magnetism so that the particles having a magnetism are separated to flow to the recycling units or the recovery unit.

13. The mass-cultivation system for microalgae of claim 9, wherein the light supply particles, the nutrient supply particles, the harmful substance adsorption particles, the $CO_2$ supply particles, and the microalgae recovery particles have a specific gravity in a predetermined range.

14. The mass-cultivation system for microalgae of claim 13, wherein the light supply particles, the nutrient supply particles, the harmful substance adsorption particles, the $CO_2$ supply particles, and the microalgae recovery particles have different specific gravities in the predetermined range so that the particles are separated to flow to the recycling units or the recovery unit.

15. The mass-cultivation system for microalgae of claim 9, wherein the light supply particles, the nutrient supply particles, the $CO_2$ supply particles, and the harmful substance adsorption particles circulate between the primary reactor and the first recycling unit, and between the secondary reactor and the second recycling unit, and wherein the microalgae recovery particles circulate between the tertiary reactor and the third recycling unit.

16. The mass-cultivation system for microalgae of claim 15, wherein the amounts of the light emitting material, the nutrient supply material, $CO_2$, and the harmful substance adsorption material that are respectively filled in the light supply particles, the nutrient supply particles, the $CO_2$ supply particles, and the harmful substance adsorption material that circulate the secondary reactor and the second recycling unit is larger than the amounts of the light emitting material, the nutrient supply material, $CO_2$, and the harmful substance adsorption material that are respectively filled in the light supply particles, the nutrient supply particles, the $CO_2$ supply particles, and the harmful substance adsorption material that circulate the primary reactor and the first recycling unit.

17. The mass-cultivation system for microalgae of claim 15, wherein each of the first and second recycling units comprises a light source or a power supply unit, and wherein the light supply particles flow to the first and second recycling units such that the light emitting material filled in the light supply particles is recycled by the light source or the power supply unit and is reintroduced into the primary reactor and the secondary reactor.

18. A mass-cultivation system for microalgae, comprising:

a reactor that contains a cultivation liquid in the interior thereof;

a recycling unit that is fluid-communicated with the reactor; and a recovery unit that is fluid-communicated with the reactor;

wherein the liquid comprises functional particles; and wherein the recycling unit includes a receiving connection from the reactor and a returning connection to the reactor;

wherein the functional particles comprise one or more of light supply particles, nutrient supply particles, harmful substance adsorption particles, $CO_2$ supply particles, and microalgae recovery particles, wherein a plurality of bosses is formed on surfaces of the microalgae recovery particles to capture cultivated microalgae, wherein the functional particles are introduced into the recycling unit by the receiving connection such that functions thereof are recycled, and then the functional particles are introduced into the reactor from the recycling unit by the returning connection, wherein the recovery unit comprises a freezer unit or a drying unit that freezes or dries the microalgae captured by the microalgae recovery particles, and wherein the recovery unit separates the captured microalgae from the microalgae recovery particles by applying ultrasonic waves or vibration to the microalgae recovery particles.

* * * * *